United States Patent [19]

Sofia

[11] Patent Number: 5,290,808
[45] Date of Patent: Mar. 1, 1994

[54] METHOD TO CONTROL THE INTAKE OF FOOD

[75] Inventor: Robert D. Sofia, Willingboro, N.J.

[73] Assignee: Carter-Wallace, Inc., New York, N.Y.

[21] Appl. No.: 973,114

[22] Filed: Nov. 6, 1992

[51] Int. Cl.5 ............................................. A61K 31/27
[52] U.S. Cl. ..................................... 514/483; 514/910
[58] Field of Search ................................. 514/483, 910

[56] References Cited

U.S. PATENT DOCUMENTS 4,978,680 12/1990 Sofia ..................................... 514/534
5,055,489 10/1991 Sofia ..................................... 514/483

Primary Examiner—Frederick E. Waddell
Assistant Examiner—M. Moezie
Attorney, Agent, or Firm—Kevin B. Clarke

[57] ABSTRACT

Novel methods and compositions for the suppression of the desire for food consumption in warm-blooded animals consisting essentially of the administration of 2-phenyl-1,3-propanediol dicarbamate are disclosed.

4 Claims, No Drawings

METHOD TO CONTROL THE INTAKE OF FOOD

The present invention relates to the discovery that 2-phenyl-1,3-propanediol dicarbamate, commonly known as felbamate, can affect the desire for food consumption in warm-blooded animals and to methods for the control of food consumption by warm-blooded animals through the administration of 2-phenyl-1,3-propanediol dicarbamate compositions to warm-blooded animals.

Felbamate is a well known pharmaceutical compound having been described in U.S. Pat. Nos. 2,884,444 and 4,868,327. Moreover, felbamate has demonstrated excellent results in the treatment and control of epileptic seizures as disclosed in U.S. Pat. No. 4,978,680, the prevention of hypoxic damage as disclosed in U.S. Pat. No. 5,055,489 and co-pending U.S. patent application Ser. No. 753,748, filed Sep. 3, 1991 now abandoned, which discloses the use of felbamate in the treatment and control of neurodegenerative disease and neuropsychopharmacological disorders.

The control of appetite is the primary goal of virtually all anti-obesity programs.

A consideration of the various components of the biopsychological system suggests that there may be many pharmacological targets, both central and peripheral, that could be exploited in order to suppress appetite. For example, if the periphery drugs could blunt positive afferent information or intensity inhibitory afferent information; they may stimulate chemoreceptor activity in the gut or modulate gastrointestinal functioning via the network of neurotransmitters in the enteric plexus. Drugs could also mimic or be substituted for appetite regulating factors in blood, alter oxidative metabolism in the liver, adjust metabolic satiety signals or change amino acid profiles. Finally, drugs could affect steroid levels reflecting energy metabolism which in turn influence neuronal function, for example corticosteroids upregulate $_2$-adrenoceptors in the paraventricular nucleus (PVN). Drugs affecting digestion or absorption can be expected to alter the timing and pattern of nutritional information reaching the brain. Within the brain, drugs are believed to alter appetite via a number of neurotransmitter and neuromodulator systems at a variety of specific sites. This complex pattern of neurochemical activity reveals the vulnerability of the appetite system to pharmacological action, and this is reflected in the large number of chemicals reported to reduce the desire for food intake. Despite this abundance of pharmaceutical activity, safe and effective appetite controlling drugs have been difficult to develop.

The influence of central neurochemical activity on the expression of appetite is complex. It involves numerous interactions between different loci and different receptors which result in shifts in the magnitude, direction and quality of eating behavior. A great deal of data has been accumulated from the direct application of chemicals to the brain either via the CSF or directly into specific sites. Most agents suppress intake but a significant number stimulate eating, sometimes in a dramatic fashion. The most frequently demonstrated action is the stimulation of feeding following activation of $_2$-adrenoceptors in the PVN. It is also known that spontaneous feeding is associated with endogenous release of noradrenaline in the PVN, and with an increase in PVN $_2$-adrenoceptor density. In turn, it appears that the PVN is a site for the long-established anorexic action of 5-HT receptor agonists. The PVN also contains glucosensitive neurons and therefore may be a point of interaction for neurotransmitter activity and metabolic states reflecting energy regulation. Circulating corticosteroids have been demonstrated to influence -adrenoceptor sensitivity and it has been argued that noradrenaline and 5-HT act antagonistically to influence the release of CRF. Since the PVN is also a potent anorectic drug binding site neurochemical activity in this area may serve to integrate behavioral, metabolic and neuroendocrine responses. In more lateral areas of the hypothalamus (perifornical zone) feeding is suppressed by micro-injection of agents that activate dopamine $D_2$ receptors or $B_2$-adrenoceptors. Noradrenaline, 5-HT and dopamine consequently produce quantitative shifts in feeding from closely related sites in the hypothalamus.

Potent feeding responses can also be obtained by micro-injection of peptides to the brain. Many peptides such as insulin, CCK, calcitonin, bombesin, neurotensin, THRH, somatostatin, VIP, CRF and glucagon suppress feeding after cerebroventricular administration. A smaller number of peptides, including B-endorphin, dynorphin, neuropeptide Y, peptide YY and galanin, increase food intake. When injected into the PVN, NPY and PYY can induce rats to eat 50% of their normal daily food intake within one hour. The stimulation of feeding by galanin appears to be specific to the PVN and closely related sites. Classic research of a decade ago indicated how projections between the brainstem and hypothalamic nuclei were involved in neuroendocrine regulation. This pattern of projections is also important for feeding; peptides such as NPY and galanin appear to originate (in part) in adrenergic or noradrenergic nuclei in the brainstem. Thus, various peptides and monoamines appear to act in concert to influence the organization of expression of appetite (and energy balance more generally). These actions are generated in response to visceral and metabolic information which reflects the immediate past history of feeding the body's nutritional status. Other neural mechanisms involving acetylcholine, benzodiazepine and GABA receptors may also be implicated at some point.

It is an object of the present invention to provide compositions for the control of the desire for food intake in warm-blooded animals.

In accordance with the present invention and for purposes of demonstrating the present invention, male Long-Evan rats (weighing 210–300 grams) were obtained from Charles River Breeding Laboratories, Kingston, N.Y. Experiments were initiated only after an acclimation period of at least four days to the animal room environment which consisted of automatically controlled illumination with 12 hours of light alternating with 12 hours of dark and controlled temperature and monitored relative humidity.

EXAMPLE

Subjects were divided into five groups of ten animals per group. Animals were housed individually in steel cages and initial body weights obtained. For 12 consecutive days, animals were fasted for 16 to 18 hours (4 p.m. to 8 or 10 a.m.) prior to dosing and then dosed orally as follows:

| Group | Treatment |
| --- | --- |
| I | Vehicle |

| Group | Treatment |
|---|---|
| II | d-amphetamine 5 mg/kg |
| III | Felbamate 100 mg/kg |
| IV | Felbamate 300 mg/kg |
| V | Felbamate 600 mg/kg |

Grain feed (Agway Prolab RMH 3200 Meal) was presented immediately after dosing in preweighed animal spill feeders. All feeders were weighed 1, 2 and 4 hours after dosing and the amount of food consumed, in grams, was recorded. Drugs and vehicle (1% acacia) were administered in a volume of 10 ml/kg body weight to animals in Groups I, II, III and IV. Drugs were administered to animals in Group V in a volume of 15 ml/kg body weight. Water was available ad libitum. Food was left in feeder cups approximately three additional hours following the fourth hour weighing, until 4 p.m. when all food was removed. At the end of day 12, animals were weighed once again to determine net gain or loss.

Student's t-test was performed to determine whether the effects of felbamate or d-amphetamine were significantly different (p 0.05) when compared with control values.

The comparative effects of felbamate on food intake in the rat are shown in Tables 1 to 3. Total food consumption for days 1 to 4 are depicted in Table 1. Each time period (1, 2 and 4 hours) indicates the total amount of food consumed as of that time, e.g., on day 1, vehicle control animals consumed a mean of 2.75 g/rat at the end of the first hour, a total of 4.41 g/rat at the end of the second hour and a total of 4.79 g/rat at the end of four hours.

On day 1, only d-amphetamine-treated animals demonstrated a significant reduction in food intake for 1, 2 and 4 hours. No significant changes in food consumption were observed in animals given 100, 300 or 600 mg/kg of felbamate.

On day 2, amphetamine-treated animals significantly reduced their food intake, whereas animals administered 100 mg/kg of felbamate showed a significant increase in food consumption for the first two hours. Animals treated with 600 mg/kg of felbamate significantly reduced their food intake 2 and 4 hours posttreatment.

On days 3 and 4, amphetamine-treated animals continued to show a significant reduction in food intake. Animals given a daily dose of 100 mg/kg of felbamate showed no significant changes in food consumption compared with the control group. However, the oral administration of 300 or 600 mg/kg of felbamate produced a significant reduction in food consumption compared with control values.

On days 5 to 8, d-amphetamine-treated animals continued to consume significantly less food compared with control animals (Table 2). During this same time period, the daily oral administration of 100 mg/kg of felbamate did no significantly alter the amount of food ingested. Daily administration of 300 mg/kg or 600 mg/kg of felbamate significantly reduced food consumption on days 5 to 8 for the latter group and on days 6 to 8 for the 300 mg/kg administered group.

From days 9 to 12, d-amphetamine-treated animals ingested significantly less food when compared with control animals (Table 3). Animals administered 100 mg/kg of felbamate generally consumed less food than controls, although only the one hour value on day 10 was significantly lower. Animals given 300 mg/kg of felbamate daily consumed significantly less food on days 9, 10 and 12 compared with controls, whereas rats receiving 600 mg/kg of felbamate daily did not consume significantly less food than control animals from the second hour on day 10 until the completion of the study on day 12.

The results of this study indicate that felbamate, when administered orally once a day for 12 days, reduces food intake in rats at doses of 300 and 600 mg/kg. The lowest dose used in this study, 100 mg/kg, had no apparent effect on food consumption.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of appetite depression desired, kind of concurrent treatment, if any, frequency of treatment and the nature of the effect desired. Usually, a daily dosage of active ingredient compound will be from about 200–1000 milligrams per day. Ordinarily, from about 250 to about 500 milligrams per day in one or more applications is effective to obtain desired results.

The active ingredient can be administered orally in solid dosage forms, such as capsules, tablets and powders, or in liquid dosage forms such as elixirs syrups and suspensions. It can also be administered parenterally in sterile liquid dosage forms.

Gelatin capsules contain the active ingredient and powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite or ascorbic acid, either alone or combined, are suitable stabilizing agents. Also used are citric acid and its salts and sodium EDTA. In addition, parenteral solutions can contain preservatives such as benzalkonium chloride, methyl- or propylparaben and chlorobutanol.

Suitable pharmaceutical carriers are described in Remington's Pharmaceutical Sciences, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose and 6 milligrams of magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs.

The percentage of 2-phenyl-1,3-propanediol dicarbamate in the compositions may be varied over wide limits and the quantity of medicament furnished by each individual tablet or capsule is relatively unimportant since the indicated total daily dose can be reached by administering either one or a plurality of capsules or tablets.

In general, an effective daily dose of the active ingredient is in the range of from about 100 milligrams to about 5 grams.

Felbamate (2-phenyl-1,3-propanediol dicarbamate) has a very favorable preclinical profile characterized by a substantial margin of safety (protective index 16.9–19.1).

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

TABLE 1

| | | Effects of Oral Administration of Felbamate on Food Consumption in the Rat | | | | | | | | | | |
|---|---|---|---|---|---|---|---|---|---|---|---|---|
| | | Total Mean Food Consumption (grams) | | | | | | | | | | |
| | | DAY 1 Hour | | | DAY 2 Hour | | | DAY 3 Hour | | | DAY 4 Hour | | |
| Treatment | n | 1 | 2 | 4 | 1 | 2 | 4 | 1 | 2 | 4 | 1 | 2 | 4 |
| Vehicle Control | 10 | 2.75 | 4.41 | 4.79 | 2.27 | 4.71 | 6.25 | 6.11 | 6.70 | 7.51 | 7.47 | 7.92 | 10.43 |
| d-Amphetamine 5 mg/kg | 10 | 0.7* | 1.82* | 2.92* | 0.43* | 0.89* | 2.98* | 2.78* | 4.23 | 7.41 | 0.2* | 1.48* | 7.34* |
| Felbamate 100 mg/kg | 10 | 3.85 | 4.27 | 5.04 | 5.44* | 7.22* | 7.82 | 6.88 | 7.38 | 8.76 | 7.25 | 8.94 | 11.7 |
| Felbamate 300 mg/kg | 10 | 3.08 | 3.75 | 4.77 | 3.04 | 3.53 | 4.77 | 3.58* | 4.20* | 4.94 | 4.36* | 4.78* | 6.77* |
| Felbamate 600 mg/kg | 10 | 3.17 | 4.06 | 4.81 | 2.14 | 2.24* | 2.52* | 1.53* | 1.82* | 2.28* | 2.41* | 2.56* | 3.58* |

*Significant p 0.05 compared to vehicle control, Student's t-test.

TABLE 2

| | | Effects of Oral Administration of Felbamate on Food Consumption in the Rat | | | | | | | | | | |
|---|---|---|---|---|---|---|---|---|---|---|---|---|
| | | Total Mean Food Consumption (grams) | | | | | | | | | | |
| | | DAY 5 Hour | | | DAY 6 Hour | | | DAY 7 Hour | | | DAY 8 Hour | | |
| Treatment | n | 1 | 2 | 4 | 1 | 2 | 4 | 1 | 2 | 4 | 1 | 2 | 4 |
| Vehicle Control | 10 | 6.07 | 6.50 | 9.65 | 8.12 | 9.27 | 13.84 | 8.11 | 10.45 | 15.65 | 6.95 | 7.84 | 8.82 |
| d-Amphetamine 5 mg/kg | 10 | 1.0* | 1.74* | 6.09* | 0.86* | 3.64* | 10.48* | 1.58* | 3.35* | 12.79* | 0.69* | 2.10* | 7.41 |
| Felbamate 100 mg/kg | 10 | 6.35 | 6.71 | 9.29 | 9.0 | 9.69 | 12.98 | 7.63 | 8.52 | 13.64 | 6.07 | 6.91 | 11.54 |
| Felbamate 300 mg/kg | 10 | 4.21 | 5.32 | 7.81 | 3.96* | 5.04* | 6.53* | 5.47* | 7.45* | 12.43 | 4.66* | 5.51 | 7.21 |
| Felbamate 600 mg/kg | 10 | 2.89* | 3.51* | 5.82* | 4.78* | 5.70* | 9.45* | 4.98* | 6.59* | 11.33* | 5.48* | 5.83* | 8.37 |

*Significant p 0.05 compared to vehicle control, Student's t-test.

TABLE 3

| Treatment | n | Effects of Oral Administration of Felbamate on Food Consumption in the Rat | | | | | | | | | | | |
|---|---|---|---|---|---|---|---|---|---|---|---|---|
| | | Total Mean Food Consumption (grams) | | | | | | | | | | | |
| | | DAY 9 Hour | | | DAY 10 Hour | | | DAY 11 Hour | | | DAY 12 Hour | | |
| | | 1 | 2 | 4 | 1 | 2 | 4 | 1 | 2 | 4 | 1 | 2 | 4 |
| Vehicle Control | 10 | 8.43 | 10.83 | 15.03 | 7.69 | 8.69 | 13.41 | 7.60 | 9.06 | 11.41 | 9.45 | 11.04 | 16.86 |
| d-Amphetamine 5 mg/kg | 10 | 1.5* | 3.02* | 9.04* | 0.87* | 2.63* | 9.73* | 0.92* | 2.15* | 11.88 | 0.94* | 4.13* | 11.31* |
| Felbamate 100 mg/kg | 10 | 7.61 | 8.43 | 11.64 | 5.79* | 7.01 | 11.21 | 6.80 | 8.24 | 11.77 | 7.44 | 9.17 | 13.69 |
| Felbamate 300 mg/kg | 10 | 5.44* | 6.08* | 9.28* | 5.53* | 6.47* | 10.26 | 6.23 | 8.17 | 13.28 | 5.62* | 6.95* | 11.65* |
| Felbamate 600 mg/kg | 10 | 4.76* | 5.51* | 8.78* | 5.55* | 8.39 | 13.70 | 7.15 | 11.34 | 17.42* | 7.81 | 10.13 | 15.09 |

*Significant p 0.05 compared to vehicle control, Student's t-test.

What is claimed is:

1. A method for the suppression of appetite and the desire for food intake which comprises administering to a human or other warm-blooded animal in need of such treatment effective amounts of the compound 2-phenyl-1,3-propanediol dicarbamate in a suitable pharmaceutical carrier.

2. A method as claimed in claim 1 which comprises administering from about 100 to about 1000 milligrams per day of 2-phenyl-1,3-propanediol dicarbamate.

3. A method as claimed in claim 1 which comprises administering from about 250 to about 500 milligrams per day of 2-phenyl-1,3-propanediol dicarbamate.

4. The method as claimed in claim 1 wherein said compound is administered orally.

* * * * *